United States Patent [19]
Stringer et al.

[11] Patent Number: 6,156,712
[45] Date of Patent: *Dec. 5, 2000

[54] CLEANING COMPOSITIONS CONTAINING A CATIONIC SURFACTANT

[75] Inventors: Orum D. Stringer, Yardley, Pa.; Robert J. Heffner, Somerset, N.J.; Clarence Robbins, Martinsville, N.J.; Barbara Thomas, Princeton, N.J.; Philip Gorlin, Monmouth Junction, N.J.

[73] Assignee: Colgate Palmolive Company, New York, N.Y.

[ * ] Notice: This patent is subject to a terminal disclaimer.

[21] Appl. No.: 09/206,923

[22] Filed: Dec. 7, 1998

Related U.S. Application Data

[63] Continuation of application No. 08/974,441, Nov. 20, 1997, Pat. No. 5,929,024.

[51] Int. Cl.$^7$ ............................ A61K 7/075; C11D 17/00; C11D 15/00

[52] U.S. Cl. ............................ 510/125; 510/417; 510/423; 510/499; 510/504

[58] Field of Search ...................................... 510/504, 417, 510/421, 423, 499, 119, 122, 123, 124, 125, 126, 235, 237; 252/547

[56] References Cited

U.S. PATENT DOCUMENTS

| | | | |
|---|---|---|---|
| 4,269,739 | 5/1981 | Gerjsner | 252/547 |
| 5,415,812 | 5/1995 | Durbut et al. | 252/547 |
| 5,714,446 | 2/1998 | Bartz et al. | 510/119 |
| 5,728,667 | 3/1998 | Richter et al. | 510/235 |

*Primary Examiner*—Yogendra Gupta
*Assistant Examiner*—Gregory E. Webb
*Attorney, Agent, or Firm*—Richard E. Nanfeldt

[57] ABSTRACT

A new class of cationic surfactants are described, wherein these cationic surfactants are an ethoxylated alkyamidoalkyldialkylammonium salt and/or an ethoxylated trialkyl ammonium salt.

14 Claims, No Drawings

CLEANING COMPOSITIONS CONTAINING A CATIONIC SURFACTANT

RELATED APPLICATION

This application is a continuation in part application of U.S. Ser. No. 08/974,441 filed Nov. 20, 1997 now U.S. Pat. No. 5,929,024.

FIELD OF THE INVENTION

This invention relates to a cleaning compositions which contain an ethoxylated alkylamidopropyldialkylammonium salt or an ethoxylated trialkyl ammonium salt.

BACKGROUND OF THE INVENTION

In recent years all-purpose liquid detergents have become widely accepted for cleaning hard surfaces, e.g., painted woodwork and panels, tiled walls, wash bowls, bathtubs, linoleum or tile floors, washable wall paper, etc. Such all-purpose liquids comprise clear and opaque aqueous mixtures of water-soluble organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No. 1,223,739.

In view of the environmentalist's efforts to reduce phosphate levels in ground water, improved all-purpose liquids containing reduced concentrations of inorganic phosphate builder salts or non-phosphate builder salts have appeared. A particularly useful self-opacified liquid of the latter type is described in U.S. Pat. No. 4,244,840.

However, these prior art all-purpose liquid detergents containing detergent builder salts or other equivalent tend to leave films, spots or streaks on cleaned unrinsed surfaces, particularly shiny surfaces. Thus, such liquids require thorough rinsing of the cleaned surfaces which is a time-consuming chore for the user.

In order to overcome the foregoing disadvantage of the prior art all-purpose liquid, U.S. Pat. No. 4,017,409 teaches that a mixture of paraffin sulfonate and a reduced concentration of inorganic phosphate builder salt should be employed. However, such compositions are not completely acceptable from an environmental point of view based upon the phosphate content. On the other hand, another alternative to achieving phosphate-free all-purpose liquids has been to use a major proportion of a mixture of anionic and nonionic detergents with minor amounts of glycol ether solvent and organic amine as shown in U.S. Pat. No. 3,935,130. Again, this approach has not been completely satisfactory and the high levels of organic detergents necessary to achieve cleaning cause foaming which, in turn, leads to the need for thorough rinsing which has been found to be undesirable to today's consumers.

Another approach to formulating hard surface or all-purpose liquid detergent composition where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of about 25 to about 800 Å in a continuous aqueous phase.

In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616—Herbots et al; European Patent Application EP 0160762—Johnston et al; and U.S. Pat. No. 4,561,991—Herbots et al. Each of these patent disclosures also teaches using at least 5% by weight of grease-removal solvent.

It also is known from British Patent Application GB 2144763A to Herbots et al, published Mar. 13,1985, that magnesium salts enhance grease-removal performance of organic grease-removal solvents, such as the terpenes, in o/w microemulsion liquid detergent compositions. The compositions of this invention described by Herbots et al. require at least 5% of the mixture of grease-removal solvent and magnesium salt and preferably at least 5% of solvent (which may be a mixture of water-immiscible non-polar solvent with a sparingly soluble slightly polar solvent) and at least 0.1% magnesium salt.

However, since the amount of water immiscible and sparingly soluble components which can be present in an o/w microemulsion, with low total active ingredients without impairing the stability of the microemulsion is rather limited (for example, up to about 18% by weight of the aqueous phase), the presence of such high quantities of grease-removal solvent tend to reduce the total amount of greasy or oily soils which can be taken up by and into the microemulsion without causing phase separation.

The following representative prior art patents also relate to liquid detergent cleaning compositions in the form of o/w microemulsions: U.S. Pat. No. 4,472,291—Rosario; U.S. Pat. No. 4,540,448—Gauteer et al; U.S. Pat. No. 3,723,330—Sheflin; etc.

Liquid detergent compositions which include terpenes, such as d-limonene, or other grease-removal solvent, although not disclosed to be in the form of o/w microemulsions, are the subject matter of the following representative patent documents: European Patent Application 0080749; British Patent Specification 1,603,047; 4,414,128; and 4,540,505. For example, U.S. Pat. No. 4,414,128 broadly discloses an aqueous liquid detergent composition characterized by, by weight:

(a) from about 1% to about 20% of a synthetic anionic, nonionic, amphoteric or zwitterionic surfactant or mixture thereof;

(b) from about 0.5% to about 10% of a mono- or sesquiterpene or mixture thereof, at a weight ratio of (a):(b) lying in the range of 5:1 to 1:3; and (c) from about 0.5% about 10% of a polar solvent having a solubility in water at 15° C. in the range of from about 0.2% to about 10%. Other ingredients present in the formulations disclosed in this patent include from about 0.05% to about 2% by weight of an alkali metal, ammonium or alkanolammonium soap of a $C_{13}$–$C_{24}$ fatty acid; a calcium sequestrant from about 0.5% to about 13% by weight; non-aqueous solvent, e.g., alcohols and glycol ethers, up to about 10% by weight; and hydrotropes, e.g., urea, ethanolamines, salts of lower alkylaryl sulfonates, up to about 10% by weight. All of the formulations shown in the Examples of this patent include relatively large amounts of detergent builder salts which are detrimental to surface shine.

U.S. Pat. No. 5,082,584 discloses a microemulsion composition having an anionic surfactant, a cosurfactant, nonionic surfactant, perfume and water; however, these compositions are not light duty liquid compositions.

The present invention relates to novel microemulsion light duty liquid detergent compositions with high foaming properties, containing a nonionic surfactant, a sulfonate surfactant, a betaine surfactant, and an ethoxylated alkyl ether sulfate surfactant.

The present invention also relates to novel light duty liquid detergent compositions with high foaming properties, containing a nonionic surfactant, or an alkali metal or ammonium sulfate surfactant in a weight ratio of nonionic surfactant to sulfate surfactant of about 3:1 to 1:1 and supplemented with lesser amounts of a Zwitterionic betaine surfactant, wherein the surfactants are dissolved in an aqueous medium.

Nonionic surfactants are in general chemically inert and stable toward pH change and are therefore well suited for mixing and formulation with other materials. The superior performance of nonionic surfactants on the removal of oily soil is well recognized. Nonionic surfactants are also known to be mild to human skin. However, as a class, nonionic surfactants are known to be low or moderate foamers. Consequently, for detergents which require copious and stable foam, the application of nonionic surfactants is limited.

The prior art is replete with light duty liquid detergent compositions containing nonionic surfactants in combination with anionic and/or betaine surfactants. As shown in U.S. Pat. No. 3,658,985 wherein an anionic based shampoo contains a minor amount of a fatty acid alkanolamide. U.S. Pat. No. 3,769,398 discloses a betaine-based shampoo containing minor amounts of nonionic surfactants. This patent states that the low foaming properties of nonionic detergents renders its use in shampoo compositions non-preferred. U.S. Pat. No. 4,329,335 also discloses a shampoo containing a betaine surfactant as the major ingredient and minor amounts of a nonionic surfactant and of a fatty acid mono- or di-ethanolamide. U.S. Pat. No. 4,259,204 discloses a shampoo comprising 0.8–20% by weight of an anionic phosphoric acid ester and one additional surfactant which may be either anionic, amphoteric, or nonionic. U.S. Pat. No. 4,329,334 discloses an anionic-amphoteric based shampoo containing a major amount of anionic surfactant and lesser amounts of a betaine and nonionic surfactants.

U.S. Pat. No. 3,935,129 discloses a liquid cleaning composition based on the alkali metal silicate content and containing five basic ingredients, namely, urea, glycerin, triethanolamine, an anionic detergent and a nonionic detergent. The silicate content determines the amount of anionic and/or nonionic detergent in the liquid cleaning composition. However, the foaming property of these detergent compositions is not discussed therein.

U.S. Pat. No. 4,129,515 discloses a heavy duty liquid detergent for laundering fabrics comprising a mixture of substantially equal amounts of anionic and nonionic surfactants, alkanolamines and magnesium salts, and, optionally, zwitterionic surfactants as suds modifiers.

U.S. Pat. No. 4,224,195 discloses an aqueous detergent composition for laundering socks or stockings comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient.

The prior art also discloses detergent compositions containing all nonionic surfactants as shown in U.S. Pat. Nos. 4,154,706 and 4,329,336 wherein the shampoo compositions contain a plurality of particular nonionic surfactants in order to effect desirable foaming and detersive properties despite the fact that nonionic surfactants are usually deficient in such properties.

U.S. Pat. No. 4,013,787 discloses a piperazine based polymer in conditioning and shampoo compositions which may contain all nonionic surfactant or all anionic surfactant.

U.S. Pat. No. 4,450,091 discloses high viscosity shampoo compositions containing a blend of an amphoteric betaine surfactant, a polyoxybutylenepolyoxyethylene nonionic detergent, an anionic surfactant, a fatty acid alkanolamide and a polyoxyalkylene glycol fatty ester. But, none of the exemplified compositions contains an active ingredient mixture wherein the nonionic detergent is present in major proportion, probably due to the low foaming properties of the polyoxybutylene polyoxyethylene nonionic detergent.

U.S. Pat. No. 4,595,526 describes a composition comprising a nonionic surfactant, a betaine surfactant, an anionic surfactant and a $C_{12}$–$C_{14}$ fatty acid monoethanolamide foam stabilizer.

SUMMARY OF THE INVENTION

The present invention relates to a new classes of cationic surfactants which are ethoxylated alkylamidoalkyidialkylammonium salts or ethoxylated trialkyl ammonium salt and their preparations.

An object of this invention is to produce a new classes of cationic surfactants which can be used in fabric care cleaning compositions, microemulsion all purpose hard surface cleaning compositions, light duty liquid cleaning compositions, microemulsion light duty liquid cleaning compositions and body care cleaning compositions.

DETAILED DESCRIPTION OF THE INVENTION

The present invention relates to all purpose hard surface cleaning compositions, light duty liquid compositions, fabric care cleaning compositions and body care cleaning compositions which contain about 0.25 wt. % to about 15 wt. % of an ethoxylated trialkyl ammonium salt, an ethoxylated alkylamidoalkyldialkylammonium salt such as ethoxylated cocoamidopropyldimethylammonium chloride.

The light duty liquid cleaning compositions of the instant invention comprise approximately by weight:
  (a) 0.5% to 40%, more preferably 1% to 30% of at least one surfactant selected from the group consisting of ethoxylated nonionics, ethoxylated glycerol type compounds, alkyl sulfates, ethoxylated alkyl ether sulfates, alkyl polyglucosides, paraffin sulfonates, olefin sulfonates, linear alkyl benzene sulfonates, sultaines and amine oxides and mixtures thereof;
  (b) 0.1% to 12%, more preferably 0.5% to 10% of an ethoxylated trialkyl ammonium salt and/or an ethoxylated alkyl amido propyl dialkyl ammonium salt;
  (c) 0.25% to 10% of at least one solubilizing agent; and
  (d) the balance being water.

The light duty liquid microemulsion cleaning compositions of the instant invention comprise approximately by weight:
  (a) 0.5% to 30%, more preferably 1% to 26% of at least one surfactant selected from the group consisting of ethoxylated nonionics, ethoxylated glycerol type compounds, alkyl sulfates, ethoxylated alkyl ether sulfates, alkyl polyglucosides, paraffin sulfonates, olefin sulfonates, linear alkyl benzene sulfonates, sultaines and amine oxides and mixtures thereof;

(b) 0.1% to 12%, more preferably 0.5% to 10% of an ethoxylated trialkyl ammonium salt and/or an ethoxylated alkyl amido propyl dialkyl ammonium salt;

(c) 0.5% to 15%, more preferably 1% to 12% of at least one cosurfactant;

(d) 0.4% to 10%, more preferably 0.5% to 8% of at least one water insoluble organic compound;

(e) 0 to 10%, more preferably 0.25% to 8% of at least one solubilizing agent; and (f) the balance being water.

The microemulsion all purpose hard surface cleaning composition of the instant invention comprises approximately by weight:

(a) 1.0% to 30%, more preferably 2% to 24% of at least one surfactant selected from the group consisting of ethoxylated nonionics, ethoxylated glycerol type compounds, alkyl sulfates, ethoxylated alkyl ether sulfates, alkyl polyglucosides, paraffin sulfonates, olefin sulfonates, linear alkyl benzene sulfonates, sultaines and amine oxides and mixtures thereof;

(b) 0.1% to 12%, more preferably 0.5% to 10% of an ethoxylated trialkyl ammonium salt and/or an ethoxylated alkyl amido propyl dialkyl ammonium salt;

(c) 1% to 15%, more preferably 1.5% to 12% of at least one cosurfactant;

(d) 0.4% to 10%, more preferably 0.5% to 8% of at least one water insoluble organic compound; and (e) the balance being water.

A typical formula for the body care cleaning composition of the instant invention comprises approximately by weight:

| Components | Formula % |
| --- | --- |
| Sodium alpha olefin sulfonate | 22.5 |
| Cocoamido propyl dimethyl 3.5 mole ethoxyl ammonium acetate (CAP 3.5 EO Quat OAc) | 0.9 |
| Lauramide DEA | 3.0 |
| Triclosan | 0.15 |
| Tetrasoium EDTA - 39% solution | 0.13 |
| Polyquaternium 7 | 0.053 |
| Glycerin | 0.01 |
| Aloe vera gel | 0.01 |
| Silk peptide and hydrolyzed silk protein | 0.08 |
| Fragrance | 0.3 |
| Color | 0.33 |
| DMDM Hydantoin | 0.40 |
| Citric acid | 0.25 |
| Sodium chloride | 1.60 |

A typical formula for the fabric care cleaning composition of the instant invention comprises approximately by weight:

| Components | Formula % |
| --- | --- |
| LAS | 9.0 |
| Cocoamido propyl dimethyl 3.5 mole ethoxyl ammonium acetate (CAP 3.5 EO Quat OAc) | 1.0 |
| AEOS | 3.4 |
| Neodol | 3.9 |
| Sodium sequicarbonate | 3.0 |

Excluded from all of the above mentioned formulas of the instant invention are natural or synthetic wax or wax like substances, fluid silicone oil with lubricating activity, fluorinated organic surface-active compounds and surface-active polysiloxane copolymer.

When both a paraffin sulfonate surfactant and an ethoxylated alkyl ether sulfate surfactant are both present in the aforementioned compositions, the weight ratio of the paraffin sulfonate to the ethoxylated alkyl ether sulfate is less than 1.5.

The water soluble nonionic surfactants utilized in this invention are commercially well known and include the primary aliphatic alcohol ethoxylates, secondary aliphatic alcohol ethoxylates, alkylphenol ethoxylates and ethyleneoxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic surfactant class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9– 15 carbon atoms, such as $C_9$–$C_{11}$ alkanol condensed with 7 to 10 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of about 8 to 15 and give good O/W emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15—S—9) or 12 EO (Tergitol 15—S—12) marketed by Union Carbide.

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic surfactants are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60–85%, preferably 70–80%, by weight. Such surfactants are commercially available from BASF-Wyandotte and a particularly preferred surfactant is a $C_{10}$–$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described composition. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic surfactants are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

The alkyl polysaccharides surfactants, which can be used have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$RO(C_nH_{2n}O)_r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferably 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucoside content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, PA. APG25 is a nonionic alkyl polyglycoside characterized by the formula:

$$C_nH_{2n+1}O(C_6H_{10}O_5)_xH$$

wherein n=10 (2%); n=12 (65%); n=14 (21–28%); n=16 (4–8%) and n=18 (0.5%) and x (degree of polymerization)= 1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The anionic surfactants which may be used in the compositions of this invention are water soluble such as triethanolamine and include the sodium, potassium, ammonium and ethanolammonium salts of linear ethoxylated $C_8$–$C_{18}$ alkyl ether sulfates, $C_8$–$C_{16}$ alkyl benzene sulfonates; $C_{10}$–$C_{20}$ paraffin sulfonates, alpha olefin sulfonates containing about 10–24 carbon atoms and $C_8$–$C_{18}$ alkyl sulfates and mixtures thereof.

The paraffin sulfonates may be monosulfonates or di-sulfonates and usually are mixtures thereof, obtained by sulfonating paraffins of 10 to 20 carbon atoms. Preferred paraffin sulfonates are those of $C_{12\text{-}18}$ carbon atoms chains, and more preferably they are of $C_{14\text{-}17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14\text{-}17}$ range will be minor and will be minimized, as will be any contents of di- or poly-sulfonates.

Examples of suitable other sulfonated anionic detergents are the well known higher alkyl mononuclear aromatic sulfonates, such as the higher alkylbenzene sulfonates containing 9 to 18 or preferably 9 to 16 carbon atoms in the higher alkyl group in a straight or branched chain, or $C_{8\text{-}15}$ alkyl toluene sulfonates. A preferred alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Preferred materials are set forth in U.S. Pat. No. 3,320,174, especially those in which the alkyls are of 10 to 13 carbon atoms.

The $C_{8\text{-}18}$ ethoxylated alkyl ether sulfate surfactants have the structure

wherein n is about 1 to about 22 more preferably 1 to 3 and R is an alkyl group having about 8 to about 18 carbon atoms, more preferably 12 to 15 and natural cuts, for example, $C_{12\text{-}14}$; $C_{12\text{-}15}$ and M is an ammonium cation or a metal cation, most preferably sodium. The ethoxylated alkyl ether sulfate is present in the composition at a concentration of about 8 to about 24 wt. %, more preferably about 10% to 22 wt. %.

The ethoxylated alkyl ether sulfate may be made by sulfating the condensation product of ethylene oxide and $C_{8\text{-}10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3 EO) sulfate.

Ethoxylated $C_{8\text{-}18}$ alkylphenyl ether sulfates containing from 2 to 6 moles of ethylene oxide in the molecule are also suitable for use in the invention compositions. These detergents can be prepared by reacting an alkyl phenol with 2 to 6 moles of ethylene oxide and sulfating and neutralizing the resultant ethoxylated alkylphenol.

The instant composition can contain a composition (herein after referred to as ethoxylated glycerol type compound) which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is Formula (I)

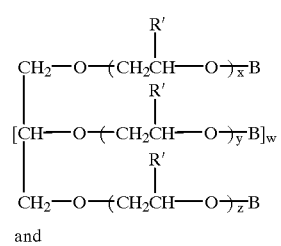

and

Formula (II)

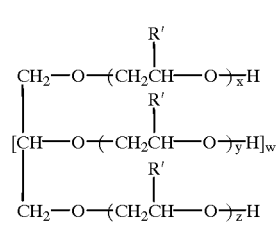

wherein w equals one to four, most preferably one. B is selected from the group consisting of hydrogen or a group represented by:

wherein R is selected from the group consisting of alkyl group having 6 to 22 carbon atoms, more preferably 11 to 15 carbon atoms and alkenyl groups having 6 to 22 carbon atoms, more preferably 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals 2 to 100, preferably 4 to 24 and most preferably 4 to 19, wherein in Formula (I) the ratio of monoester/diester/triester is 45 to 90/5 to 40/1 to 20, more preferably 50 to 90/9 to 32/1 to 12, wherein the ratio of Formula (I) to Formula (II) is a value between 3 to 0.02, preferably 3 to 0.1, most preferably 1.5 to 0.2, wherein it is most preferred that there is more of Formula (II) than Formula (I) in the mixture that forms the compound.

The ethoxylated glycerol type compound used in the instant composition is manufactured by the KAO Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than 1.7, more preferably less than 1.5 and most preferably less than 1.0. The ethoxylated glycerol type compound has a molecular weight of 400 to 1600, and a pH (50 grams/liter of water) of 5–7. The Levenol compounds are substantially non irritant to human skin and have a primary biodegradabillity higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxicity values of algae growth inhibition>100 mg/liter; acute toxicity for Daphniae>100 mg/liter and acute fish toxicity>100 mg/liter. The Levenol compounds have a ready biodegradability higher than 60% which is the minimum required value according to OECD 301 B measurement to be acceptably biodegradable.

Polyesterified nonionic compounds also useful in the instant compositions are Crovol PK-40 and Crovol PK-70 manufactured by Croda GMBH of the Netherlands. Crovol PK-40 is a polyoxyethylene (12) Palm Kernel Glyceride which has 12 EO groups. Crovol PK-70 which is preferred is a polyoxyethylene (45) Palm Kernel Glyceride have 45 EO groups.

The preferred amine oxide is cocoamido-propylamine oxide. The amine oxide which can be used in the instant composition is depicted by the formula:

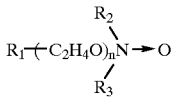

wherein $R_1$ is an alkyl, 2-hydroxyalkyl, 3-hydroxyalkyl, or 3-alkoxy-2-hydroxypropyl radical in which the alkyl and alkoxy, respectively, contain from about 8 to about 18 carbon atoms; $R_2$ and $R_3$ are each methyl, ethyl, propyl, isopropyl, 2-hydroxyethyl, 2-hydroxypropyl, or 3-hydroxypropyl; and n is from 0 to about 10. Particularly preferred are amine oxides of the formula:

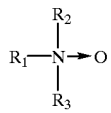

wherein $R_1$ is a $C_{12-18}$ alkyl and $R_2$ and $R_3$ are methyl or ethyl. The above ethylene oxide condensates, amides, and amine oxides are more fully described in U.S. Pat. No. 4,316,824 (Pancheri), incorporated herein by reference. An especially preferred amine oxide is depicted by the formula:

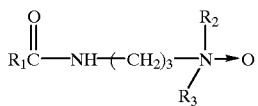

wherein $R_1$ is a saturated or unsaturated alkyl group having about 6 to about 24 carbon atoms, $R_2$ is a methyl group, and $R_3$ is a methyl or ethyl group. The preferred amine oxide is cocoamidopropyl-dimethylamine oxide.

The composition also contains a sultaine which is preferably a cocoamidopropylhydroxy sultaine. The sultaine can be depicted by the formula:

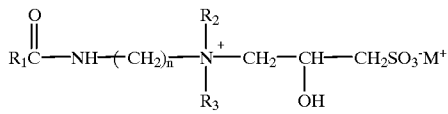

wherein $R_1$ is a saturated or unsaturated alkyl group having about 6 to about 24 carbon atoms, $R_2$ is a methyl or ethyl group, $R_3$ is a methyl or ethyl group, n is about 1 to about 6, and $M^+$ is an alkali metal cation. The most preferred hydroxysultaine is a potassium salt of cocoamidopropyl hydroxysultaine.

The quaternary ammonium complexes which are ethoxylated trialkyl ammonium salt and/or an ethoxylated alkyl amido propyl dialkyl ammonium salt are selected from the group consisting of:

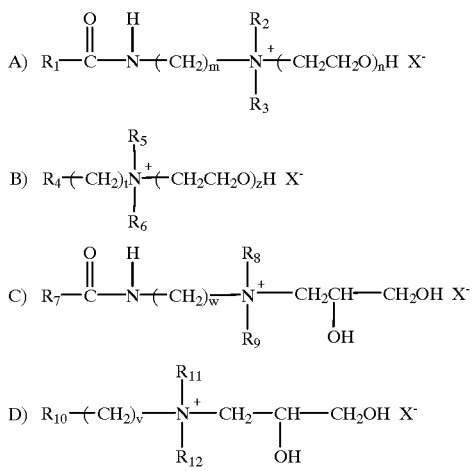

wherein $R_1$, $R_4$, $R_7$ and $R_{10}$ are a $C_6$ to $C_{18}$ alkyl group, especially preferred are a coco or a tallow group or a $C_8$ alkyl group; m, t, w and v are independently selected numbers from 2 to 20, preferably 3 to 5; $R_2$, $R_3$, $R_5$, $R_6$, $R_8$, $R_9$, $R_{11}$ and $R_{12}$ are independently selected $C_1$ to $C_3$ alkyl groups and n and z are each a number equal from 1 to 5 and X⁻ is an anionic group selected from the group consisting of chloride, sulfate, bromide, nitrate and acetate. An especially preferred ethoxylated alkylamidoalkyldialkylammonium salt is an ethoxylated cocoamidopropyldimethylammonium chloride.

The water insoluble saturated or unsaturated organic compound used which can be in the microemulsion is used at a concentration of about 1.0 wt. % to about 8 wt. %, more preferably about 2.0 wt. % to about 7 wt. %. The water insoluble saturated or unsaturated organic compound is selected from the group consisting of water insoluble hydrocarbons containing a cycloalkyl group having 5 to 10 carbon atoms, wherein the alkyl or cycloalkyl group can be saturated or unsaturated and the cycloalkyl group can have one or more saturated or unsaturated alkyl groups having 1 to 20 carbon atoms affixed to the alkyl or cycloalkyl group and one or more halogens, alcohols, nitro or ester group substituted on the cycloalkyl group or alkyl group; aromatic hydrocarbons; water insoluble ethers; water insoluble carboxylic acids, water insoluble alcohols, water insoluble amines, water insoluble esters, nitropropane, 2,5dimethylhydrofuran, 2-ethyl2-methyl 1,3dioxolane, 3-ethyl 4-propyl tetrahydropyran, N-isopropyl morpholine, alpha-methyl benzyldimethylamine, methyl chloraform and methyl perchlorapropane, and mixtures thereof. Typical hydrocarbons are cyclohexyl-1decane, methyl-3 cyclohexyl-9 nonane, methyl-3 cyclohexyl-6 nonane, dimethyl cycloheplane, trimethyl cyclopentane, ethyl-2 isopropyl-4 cyclohexane. Typical aromatic hydrocarbons are bromotoluene, diethyl benzene, cyclohexyl bromoxylene, ethyl-3 pentyl-4 toluene, tetrahydronaphthalene, nitrobenzene, and methyl naphthalene. Typical water insoluble esters are benzyl acetate, dicyclopentadienylacetate, isononyl acetate, isobornyl acetate and isobutyl isobutyrate. Typical water insoluble ethers are di(alphamethyl benzyl) ether, and diphenyl ether. A typical alcohol is phenoxyethanol. A typical water insoluble nitroderivative is nitro propane.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, TM Vanilin, Vetyver oil (Java), Wintergreen, Allocimene, Arbanex™, Arbanol®), Bergamot oils, Camphene, Alpha-Campholenic aldehyde, I-Carvone, Cineoles, Citral, Citronellol Terpenes, Alpha-Citronellol, Citronellyl Acetate, Citronellyl Nitrile, Para-Cymene, Dihydroanethole, Dihydrocarveol, d-Dihydrocarvone, Dihydrolinalool, Dihydromyrcene, Dihydromyrcenol, Dihydromyrcenyl Acetate, Dihydroterpineol, Dimethyloctanal, Dimethyloctanol, Dimethyloctanyl Acetate, Estragole, Ethyl-2 Methylbutyrate, Fenchol, Fernlol™, Florilys™, Geraniol, Geranyl Acetate, Geranyl Nitrile, Glidmint™ Mint oils, Glidox™, Grapefruit oils, trans-2-Hexenal, trans-2-Hexenol, cis-3-Hexenyl Isovalerate, cis-3-Hexanyl-2-methylbutyrate, Hexyl Isovalerate, Hexyl-2-methylbutyrate, Hydroxycitronellal, Ionone, Isobornyl Methylether, Linalool, Linalool Oxide, Linalyl Acetate, Menthane Hydroperoxide, I-Methyl Acetate, Methyl Hexyl Ether, Methyl-2-methylbutyrate, 2-Methylbutyl Isovalerate, Myrcene, Nerol, Neryl Acetate, 3-Octanol, 3-Octyl Acetate, Phenyl Ethyl-2-methylbutyrate, Petitgrain oil, cis-Pinane, Pinane Hydroperoxide, Pinanol, Pine Ester, Pine Needle oils, Pine oil, alpha-Pinene, beta-Pinene, alpha-Pinene Oxide, Plinol, Plinyl Acetate, Pseudo Ionone, Rhodinol, Rhodinyl Acetate, Spice oils, alpha-Terpinene, gamma-Terpinene, Terpinene-4-OL, Terpineol, Terpinolene, Terpinyl Acetate, Tetrahydrolinalool, Tetrahydrolinalyl Acetate, Tetrahydromyrcenol, Tetralol®, Tomato oils, Vitalizair, Zestoral™.

The at least one solubilizing agent can be sodium xylene sulfonate, sodium cumene sulfonate, a $C_{2-3}$ mono or dihydroxy alkanols such as ethanol, isopropanol and propylene glycol and mixtures thereof. The solubilizing agents are included in order to control low temperature cloud clear properties in a composition containing a solubilizing agent, urea can be optionally employed in the instant composition as a supplemental solubilizing agent at a concentration of 0 to about 10 wt. %, more preferably about 0.5 wt. % to about 8 wt. %.

Preferably the solubilizing ingredient will be a mixture of ethanol and a water soluble salt of a $C_1$–$C_3$ substituted benzene sulfonate hydrotrope such as sodium xylene sulfonate or sodium cumene sulfonate or a mixture of said sulfonates or ethanol and urea. Inorganic alkali metal or alkaline earth metal salts such as sodium sulfate, magnesium sulfate, sodium chloride and sodium citrate can be added at concentrations of 0.5 to 4.0 wt. % to modify the cloud point of the nonionic surfactant and thereby control the haze of the resultant solution.

The instant composition can contain as a solubilizing agent a $C_{12-14}$ alkyl monoalkanol amide such as lauryl monoalkanol amide and/or a $C_{12-14}$ alkyl dialkanol amide such as lauryl diethanol amide or coco diethanol amide and wherein the concentration of the mono- and/or di-alkanol amide is about 0 to about 6 wt. %, more preferably about 1 wt. % to about 5 wt. %. The instant composition can contain about 0 wt. % to about 6 wt. %, more preferably about 1 wt. % to about 5 wt. % of an ethoxylated $C_{12-14}$ alkyl monoalkanol amide which has amount 2 to about 8 ethoxylate groups.

The major class of compounds found to provide highly suitable cosurfactants for use in the microemulsion compositions are water-soluble polyethylene glycols having a molecular weight of 150 to 1000, polypropylene glycol of the formula $HO(CH_3CHCH_2O)_nH$ wherein n is a number from 2 to 18, mixtures of polyethylene glycol and polypropyl glycol (Synalox) and mono and di $C_1$–$C_6$ alkyl ethers and esters of ethylene glycol and propylene glycol having the structural formulas $R(X)_nOH$ $R_1(X)_nOH$ $R(X)_nOR$ and $R_1(X)_nOR_1$ wherein R is $C_1$–$C_6$ alkyl group, $R_1$ is $C_2$–$C_4$ acyl group, X is $(OCH_2CH_2)$ or $(OCH_2(CH_3)CH)$ and n is a number from 1 to 4, diethylene glycol, triethylene glycol, an alkyl lactate, wherein the alkyl group has 1 to 6 carbon atoms, 1methoxy-2-propanol, 1 methoxy-3-propanol, and 1 methoxy 2-, 3- or 4-butanol.

Representative members of the polypropylene glycol include dipropylene glycol and polypropylene glycol having a molecular weight of 150 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate. When these glycol type cosurfactants are at a concentration of about 1.0 to about 14 weight %, more preferably about 2.0 weight % to about 10 weight % in combination with a water insoluble hydrocarbon at a concentration of at least 0.5 weight %, more preferably 1.5 weight % one can form a microemulsion composition.

While all of the aforementioned glycol ether compounds provide the described stability, the most preferred cosurfactant compounds of each type, on the basis of cost and cosmetic appearance (particularly odor), are dipropylene glycol monomethyl ether and diethylene glycol monobutyl ether. Other suitable water insoluble cosurfactants are water soluble esters such as ethyl lactate and water soluble carbohydrates such as butyl glycosides.

In addition to the above-described essential ingredients required for the formation of the instant compositions, the compositions of this invention may often and preferably do contain one or more additional ingredients which serve to improve overall product performance.

One such ingredient is an inorganic or organic salt of oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level. Thus, depending on such factors as the pH of the system, the nature of the primary surfactants and cosurfactant, and so on, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

Preferably, in the dilute compositions the metal compound is added to the composition in an amount sufficient to provide at least a stoichiometric equivalence between the anionic surfactant and the multivalent metal cation. For example, for each gram-ion of $Mg^{++}$ there will be 2 gram moles of paraffin sulfonate, alkylbenzene sulfonate, etc., while for each gram-ion of $Al^{3+}$ there will be 3 gram moles of anionic surfactant. Thus, the proportion of the multivalent salt generally will be from 0 to about 6 wt. %, more preferably about 1 to about 5 wt. %.

In addition to the previously mentioned essential and optional constituents of the instant compositions, one may also employ normal and conventional adjuvants, provided they do not adversely affect the properties of the detergent. Thus, there may be used various coloring agents and perfumes; ultraviolet light absorbers such as the Uvinuls, which are products of GAF Corporation; sequestering agents such as ethylene diamine tetraacetates; magnesium sulfate heptahydrate; pearlescing agents and opacifiers; pH modifiers; etc. The proportion of such adjuvant materials, in total will normally not exceed 15% of weight of the detergent composition, and the percentages of most of such individual components will be a maximum of 5% by weight and preferably less than 2% by weight. Sodium formate can be included in the formula as a perservative at a concentration of 0.1 to 4.0%. Sodium bisulfite can be used as a color stabilizer at a concentration of 0.01 to 0.2 wt. %.

The fabric care cleaning composition can contain a detergent builder salt. Specific examples of detergent builder salts include the polyphosphates, such as alkali metal pyrophosphate, alkali metal tripolyphosphate, alkali metal metaphosphate, and the like, for example, sodium or potassium tripolyphosphate (hydrated or anhydrous), tetrasodium or tetrapotassium pyrophosphate, sodium or potassium hexa-metaphosphate, trisodium or tripotassium orthophosphate and the like, sodium or potassium carbonate, sodium or potassium citrate, sodium or potassium nitrilotriacetate, and the like. The phosphate builders, were not precluded due to local regulations, are preferred and mixtures of tetrapotassium pyrophosphate (TKPP) and sodium tripolyphosphate (NaTPP) (especially the hexahydrate) are especially preferred. Typical ratios of NaTPP to TKPP are from 2:1 to 1:8, especially from 1:1.1 to 1:6. The total amount of detergent builder salts is preferably from 5 to 35% by weight, more preferably from 15 to 35%, especially from 18 to 30% by weight of the composition.

The following examples are meant to be illustrative of the invention and are expressed in weight % unless otherwise specified.

EXAMPLE 1

Cocoamido propyl dimethyl 3 mole ethoxyl ammonium salt was prepared by one of the following procedures.

Method 1:

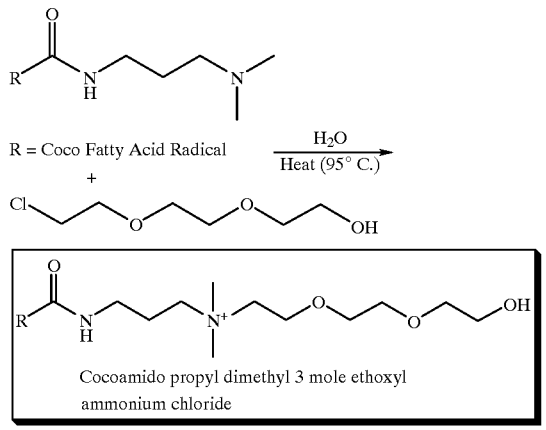

A mixture of water (203 mL) containing cocoamidopropydimethylamine (85.8 g, 0.296 moles) and 2-[2-(2-chloroethoxy)ethanol (50 g, 0.296 moles) was heated at reflux (95 to 100° C.) for 12 hours. During this time the reaction went from a turbid mixture to a clear solution providing a maximum conversion of 91 mole % of the cocoamido propyl dimethyl 3 mole ethoxyl ammonium chloride (CAP 3 EO Quat), based on $^1$H-NMR assay. The reaction was a allowed to cool to room temperature where it formed a thick gel. Based on the purity specifications of the starting materials and the $^1$H-NMR assay of the final reaction mixture, the following analysis was approximated:

| | |
|---|---|
| Water | 58% |
| Cocoamido propyl dimethyl 3 mole ethoxyl ammonium chloride | 33% |
| Cocoamidopropyldimethylamine | 5% |
| Glycerine | 2% |
| 2-[2-(2-Chloroethoxy)ethoxy]-ethanol | 2% |
| N,N-Diemethylaminopropylamine | 0.1% |

Method 2:

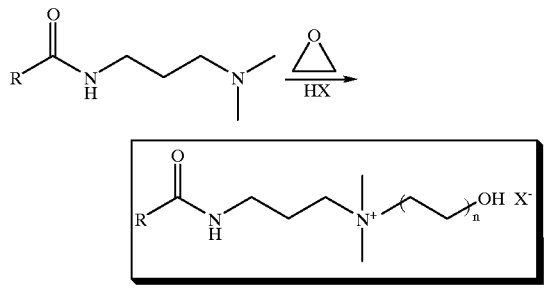

A mixture of approximately 16.5% glacial acetic acid was mixed with 83.5% cocoamidopropydimethylamine. That mixture was then ethoxylated with 3.5 moles of ethylene oxide. At the end of the reaction, excess ethylene oxide and dioxane were removed from the reactor by distillation to provide a free flowing, and pourable liquid of the CAP 3.5 EO Quat. Based on the purity specifications of the starting materials and the $^1$H-NMR assay of the final reaction mixture, the following analysis was approximated:

| | |
|---|---|
| Cocoamido propyl dimethyl 3.5 mole ethoxyl ammonium acetate | 97% |
| Cocoamidopropyldimethylamine | $^2$1% |
| Glycerine | 2% |

EXAMPLE 3

Dodecyl dimethyl 3 mole ethoxyl ammonium salt was prepared by the following procedure.

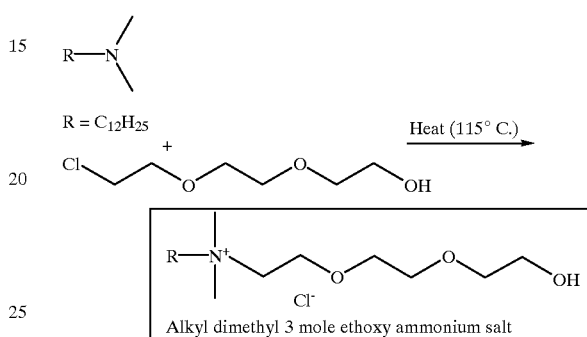

A mixture of dodecyidimethylamine (50 g, 0.230 moles) and 2-[2-(2-chloroethoxy)ethanol (39.5 g, 0.230 moles) in water (220 mL) was heated at 95° C. After 12 hours the reaction was allowed to cool to room temperature providing an 87% yield of the dodecyl dimethyl 3 mole ethoxyl ammonium chloride, based on $^1$H-NMR assay.

EXAMPLE 4

Cocoamidopropyl dimethyl 3 mole glycerinyl ammonium salt was prepared by the following procedure.

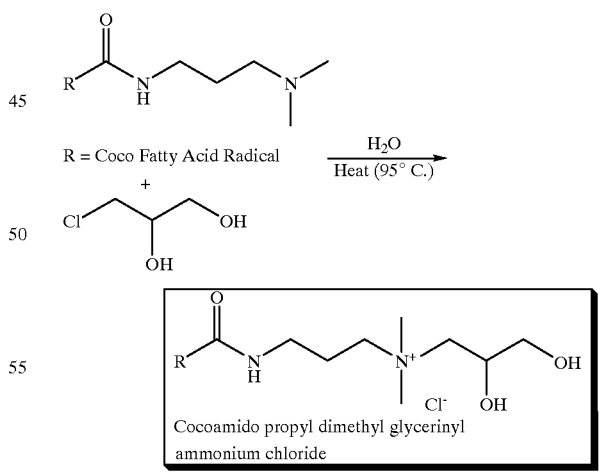

A mixture of dodecyldimethylamine (40 g, 0.138 moles) and 3-chloro-1,2-propanediol (15.2 g, 0.138 moles) were heated together neat (without solvent) at 120° C. After 12 hours the reaction was allowed to cool to room temperature providing an 93% yield of the dodecyl dimethyl glycerinyl ammonium chloride, based on $^1$H-NMR assay.

EXAMPLE 5

The following light duty liquid (LDL) formulas were made at 25° C. by simple mixing. Each of the following formulas were evaluated for skin mildness using the Zein test. Zein test scores are listed in the following.

| Formula | A | B | C | D | E |
|---|---|---|---|---|---|
| Sodium linear alkyl benzene sulfonate | 12.01 | 12.01 | 12.01 | 12.01 | 12.01 |
| Ethoxylated C8–C18 alkyl ether sulfate 1.3 EO | 10.64 | 10.64 | 10.64 | 10.64 | 10.64 |
| APG 625 | 10.0 | 10.0 | 10.0 | 10.0 | 10.0 |
| Cocoamido propyl dimethyl amine oxide | 6.34 | | | | |
| CAP 3 EO Quat | | 6.34 | | | |
| $C_{12}$ 3 EO Quat | | | 6.34 | | |
| CAP Diol Quat | | | | 6.34 | |
| $C_{12}$ Diol Quat | | | | | 6.34 |
| Sodium cumene sulfonate | 2 | 2 | 2 | 2 | 2 |
| Zein Score | 23.0 | 18.2 | 19.8 | 18.7 | 14.0 |

The Zein test is an in vitro irritation test. A 4% detergent solution is mixed with Zein protein (from corn), filtered, and incubated with a protein assay. The amount of protein dissolved by the detergent is then measured spectroscopically and converted into the Zein score. The amount of solubilized Zein is dependent upon the skin compatibility of the surfactants. The higher the Zein score, the more irritating the surfactant solution or detergent. For comparison, a 1% sodium lauryl sulfate solution gives a Zein score of 38.7.

EXAMPLE 6

The following shampoo formulas were made at 25° C. by simple mixing. Each of the following formulas were evaluated for skin mildness using the Zein test. The formulations containing the cocoamido propyl dimethyl 3 and 2 mole ethoxyl ammonium salts (CAP 3 EO and 2 EO Quat) exhibit mildness compared to straight SLS and SLS with CAP Betaine.

| Formula | A | B | C | D | E | F | G | H |
|---|---|---|---|---|---|---|---|---|
| % sodium linear alkyl benzene sulfonate | 1 | 1 | 1 | 1 | 1 | 1 | 1 | |
| % cocoamido propyl dimethyl 3EO Quat | 0.5 | 1 | | | | | | |
| % cocoamido propyl dimethyl 2EO Quat | | | 0.5 | 1 | | | | |
| % cocoamido propyl dimethyl Betaine | | | | | 0.5 | 1.0 | | |
| % H2O | 98.5 | 98.0 | 98.5 | 98.0 | 98.5 | 98.0 | 99.0 | 100 |
| Zien Score | 19 | 5.9 | 19 | 0.04 | 27.6 | 20.6 | 30.6 | 1.2 |

EXAMPLE 7

The following formulas were made at 25° C. by simple mixing:

| Raw Material | A | B | C |
|---|---|---|---|
| Cocoamido propyl dimethyl 3EO Quat | 2.00 | 1.3 | — |
| Cocoamido propyl dimethyl 2E O Quat | — | — | 1.3 |
| Paraffin sulfonate | 2.00 | | |
| NaLAS | | 5.5 | 5.5 |
| DEGMBE | 3.5 | 4.5 | 4.5 |
| MgSO4 7H2O | 0.0 | 0.0 | 0.0 |
| Perfume | 0.8 | 0.8 | 0.8 |
| Water | Bal. | Bal. | Bal. |
| pH | 6.55 | 7 | 7 |
| Appearance | clear, 1 phase | clear, 1 phase | clear, 1 phase |

The above formulas were tested using the standard APC cleaning protocol. This test involves cleaning red grease from a Formica tile using a Gardner Abrader. These formulas were compared with a commercial Ajax microemulsion composition produced in France. The cleaning formulations were tested neat on a sponge. The change in reflectance was measured after 8 cycles of the abrader and used to calculate % cleaning. At least 3 replicates were run for each formulation. The data was then normalized such that Ajax has a cleaning index of 100.

| Cleaning Index | |
|---|---|
| Formula | Index |
| Ajax | 100 |
| 1C | 128 |
| 3B | 131 |
| 4B | 134 |

All the formulas showed better performance that the Ajax standard.

EXAMPLE 8

To demonstrate that the instant compositions exhibit improved fabric cleaning the following tests were conducted.

To each 1 liter bucket of a six bucket terg-o-tometer was added 0.57 grams of total surfactant, but with differing weight ratios of linear alkyl benzene sodium sulfonate (LAS) to cocamido propyl dimethyl 3 mole ethoxy ammonium chloride (CAP 3 EO Quat) of Example 1. Bucket # 1 contained an LAS to CAP 3 EO Quat ratio of 100 to 0, bucket # 2 contained a 95 LAS to 5 CAP 3 EO Quat ratio, bucket # 3 contained a ratio of 90 to 10, bucket # 4 contained a ratio of 85 to 15, Bucket # 5 contained a ratio of 80 to 20, and bucket # 6 contained an LAS to CAP 3 EO Quat ratio of 0 to 100. Once the surfactants had been added, 6 mL of a 25,000 ppm solution of $CaCO_3$ is added to bring hardness to the 150 ppm level after final dilution with water. This is followed by the addition of 15 mL of a 162,000 ppm of base bead. Each bucket of the six bucket tergotometer was diluted to 1 kilogram with deionized water followed by equilibration of the system to the desired temperature of 77° F. At the desired temperature the soiled swatch sets of particulate soils and oily soils were added to each terg bucket and allowed to agitate for 10 minutes at 100 rpm, after which the swatches were removed and rinsed in tap water at ambient temperature. The wet swatches were dried by placing each swatch set on two paper towels and allowed them to air dry. The swatches were then read by a reflectometer to measure a % soil removal value for each individual soil where by an overall % soil removal value was determined. These results are presented in tabulated form in the following tables.

The % soil removal values of LAS as compared to mixtures of LAS and triethoxylated cocoamidopropyldiemthylammonium chloride CAP 3 EO Quat on oily soils at 77° F.

| System | Spangler Sebum (65D/35C) | Liquid Makeup (65D/35C) | Spangler Sebum (Spun Nylon) | Average of 3-Soils |
|---|---|---|---|---|
| LAS/CAP 3 EO (100 to 0) | 69 | 77 | 92 | 79 |
| LAS/CAP 3 EO (95 to 5) | 80 | 77 | 100 | 86 |
| LAS/CAP 3 EO (90 to 10) | 78 | 69 | 99 | 82 |
| LAS/CAP 3 EO (85 to 15) | 75 | 67 | 97 | 80 |
| LAS/CAP 3 EO 80 to 20 | 72 | 63 | 93 | 76 |

The % soil removal values of LAS as compared to mixtures of LAS and triethoxylated cocoamidopropyidiemthylammonium chloride CAP 3 EO Quat on particulate soils at 77° F.

| System | Piscataway Clay (Cotton Percale) | Potting Soil (Poplin) | Bandy Black Clay (Poplin) | Average of 3-Soils |
|---|---|---|---|---|
| LAS/CAP 3 EO (100 to 0) | 59 | 65 | 85 | 70 |
| LAS/CAP 3 EO (95 to 5) | 66 | 72 | 92 | 77 |
| LAS/CAP 3 EO (90 to 10) | 67 | 72 | 92 | 77 |
| LAS/CAP 3 EO (85 to 15) | 64 | 70 | 90 | 75 |
| LAS/CAP 3 EO (80 to 20) | 64 | 70 | 87 | 74 |

What is claimed:

1. A light duty liquid cleaning composition comprising approximately by weight:

(a) 0.5% to 40% of at least one surfactant selected from the group consisting of ethoxylated nonionics, ethoxylated glycerol type compounds, alkyl sulfates, ethoxylated alkyl ether sulfates, alkyl polyglucosides, paraffin sulfonates, olefin sulfonates, linear alkyl benzene sulfonates, sultaines and amine oxides and mixtures thereof;

(b) 0.1% to 12% of a quaternary ammonium complex wherein the quaternary complex is selected from the group consisting of:

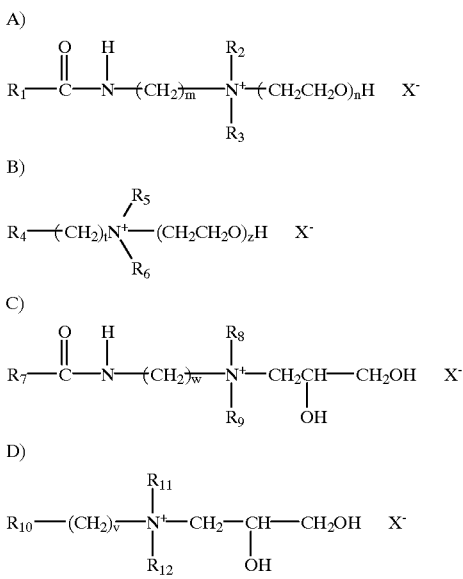

wherein $R_1$, $R_4$, $R_7$ and $R_{10}$ are each a $C_6$ to $C_{18}$ alkyl group, m, t, w and v are each a number from 2 to 20, $R_2$, $R_3$, $R_5$, $R_6$, $R_8$, $R_9$, $R_{11}$ and $R_{12}$ are each a $C_1$ to $C_3$ alkyl groups and n and z are each a number equal from 1 to 5 and $X^-$ is an anionic group selected from the group consisting of chloride, sulfate, bromide, nitrate and acetate; and (c) the balance being water, wherein if both a paraffin sulfonate and an ethoxylated alkyl ether sulfate are present in the composition, the weight ratio of paraffin sulfonate to the ethoxylated alkyl ether sulfate is less than one and the composition does not contain a fluorinated organic surface active compound.

2. A light duty liquid microemulsion composition comprising approximately by weight:

(a) 0.5% to 30% of at least one surfactant selected from the group consisting of ethoxylated nonionics, ethoxylated glycerol type compounds, alkyl sulfates, ethoxylated alkyl ether sulfates, alkyl polyglucosides, paraffin sulfonates, olefin sulfonates, linear alkyl benzene sulfonates, sultaines and amine oxides and mixtures thereof;

(b) 0.1% to 12% of a quaternary ammonium complex wherein the quaternary complex is selected from the group consisting of:

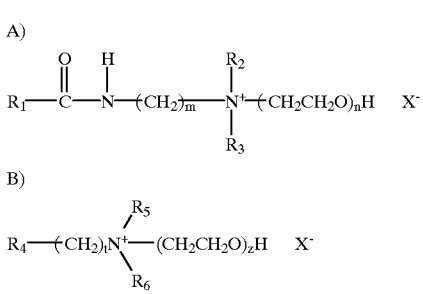

-continued

C)

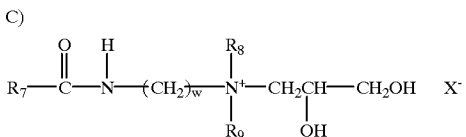

D)

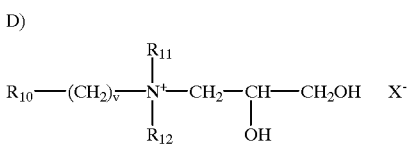

wherein $R_1$, $R_4$, $R_7$ and $R_{10}$ are each a $C_6$ to $C_{18}$ alkyl group, m, t, w and v are each a number from 2 to 20, $R_2$, $R_3$, $R_5$, $R_6$, $R_8$, $R_9$, $R_{11}$ and $R_{12}$ are each a $C_1$ to $C_3$ alkyl groups and n and z are each a number equal from 1 to 5 and $X^-$ is an anionic group selected from the group consisting of chloride, sulfate, bromide, nitrate and acetate; and (c) 0.5% to 15% of at least one cosurfactant;
(d) 0.4% to 10% of at least one water insoluble organic compound;
(e) 0 to 10% of at least one solubilizing agent; and
(f) the balance being water, wherein if both a paraffin sulfonate and an ethoxylated alkyl ether sulfate are present in the composition, the weight ratio of paraffin sulfonate to the ethoxylated alkyl ether sulfate is less than one and the composition does not contain a fluorinated organic surface active compound.

3. The composition of claim 2, wherein said solubilizing agent is a $C_{2-4}$ mono or dihydroxy alkanol.

4. The composition of claim 2, wherein said solubilizing agent is selected from the group consisting of isopropanol, ethanol and propylene glycol and mixtures thereof.

5. The composition of claim 4, containing a supplemental solubilizing agent which is urea.

6. The composition of claim 2, wherein said cosurfactant is selected from the group consisting of glycerol, polyethylene glycols, polypropylene glycol of the formula $HO(CH_3)CHCH_2O)_nH$, wherein n is 2 to 18, mixtures of polyethylene glycol and polypropylene glycol, mono $C_1$–$C_6$ alkyl ethers and esters of ethylene glycol and propylene glycol having the formulas of $R(X)_nOH$ and $R_1(X)_nOH$ wherein R is a $C_{1-6}$ alkyl group, $R_1$ is a $C_{2-4}$ acyl group, X is $(OCH_2CH_2)$ or $(OCH_2CHCH_3)$ and n is from 1 to 4.

7. The composition of claim 2, wherein said cosurfactant is selected from the group consisting of polypropylene glycol of the formula $HO(CH_3CHCH_2O)_nH$, wherein n is 2 to 18, mono $C_1$–$C_6$ alkyl ethers and esters of ethylene glycol and propylene glycol having the formulas of $R(X)_nOH$ and $R_1(X)_nOH$ wherein R is a $C_{1-6}$ alkyl group, $R_1$ is a $C_{2-4}$ acyl group, X is $(OCH_2CH_2)$ or $(OCH_2CHCH_3)$ and n is from 1 to 4.

8. The composition of claim 2, wherein said cosurfactant is dipropylene glycol monomethyl ether.

9. The composition of claim 2, wherein said cosurfactant is diethylene glycol monobutyl ether.

10. An all purpose microemulsion cleaning composition comprising approximately by weight:
(a) 1.0% to 30% of at least one surfactant selected from the group consisting of ethoxylated nonionics, ethoxylated glycerol type compounds, alkyl sulfates, ethoxylated alkyl ether sulfates, alkyl polyglucosides, paraffin sulfonates, olefin sulfonates, linear alkyl benzene sulfonates, sultaines and amine oxides and mixtures thereof;
(b) 0.1% to 12% of a quaternary ammonium complex wherein the quaternary complex is selected from the group consisting of:

A)

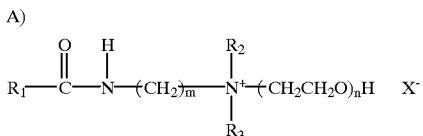

B)

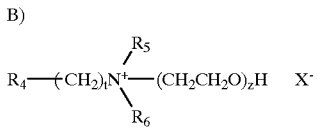

C)

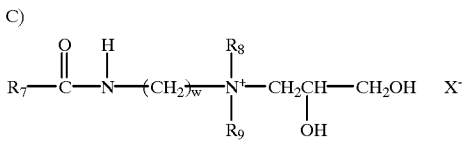

D)

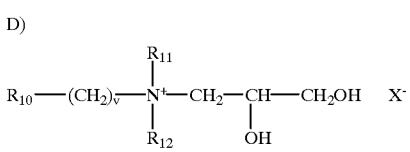

wherein $R_1$, $R_4$, $R_7$ and $R_{10}$ are each a $C_6$ to $C_{18}$ alkyl group, m, t, w and v are each a number from 2 to 20, $R_2$, $R_3$, $R_5$, $R_6$, $R_8$, $R_9$, $R_{11}$ and $R_{12}$ are each a $C_1$ to $C_3$ alkyl groups and n and z are each a number equal from 1 to 5 and $X^-$ is an anionic group selected from the group consisting of chloride, sulfate, bromide, nitrate and acetate; and (c) 0.5% to 15% of at least one cosurfactant;
(d) 0.4% to 10% of at least one water insoluble organic compound;
(e) 0 to 10% of at least one solubilizing agent; and
(f) the balance being water, wherein if both a paraffin sulfonate and an ethoxylated alkyl ether sulfate are present in the composition, the weight ratio of paraffin sulfonate to the ethoxylated alkyl ether sulfate is less than one and the composition does not contain a fluorinated organic surface active compound.

11. The composition of claim 10, wherein said cosurfactant is selected from the group consisting of glycerol, polyethylene glycols, polypropylene glycol of the formula $HO(CH_3)CHCH_2O)_nH$, wherein n is 2 to 18, mixtures of polyethylene glycol and polypropylene glycol, mono $C_1$–$C_6$ alkyl ethers and esters of ethylene glycol and propylene glycol having the formulas of $R(X)_nOH$ and $R_1(X)_nOH$ wherein R is a $C_{1-6}$ alkyl group, $R_1$ is a $C_{2-4}$ acyl group, X is $(OCH_2CH_2)$ or $(OCH_2CHCH_3)$ and n is from 1 to 4.

12. The composition of claim 10, wherein said cosurfactant is selected from the group consisting of polypropylene glycol of the formula $HO(CH_3CHCH_2O)_nH$, wherein n is 2 to 18, mono $C_1$–$C_6$ alkyl ethers and esters of ethylene glycol and propylene glycol having the formulas of $R(X)_nOH$ and $R_1(X)_nOH$ wherein R is a $C_{1-6}$ alkyl group, $R_1$ is a $C_{2-4}$ acyl group, X is $(OCH_2CH_2)$ or $(OCH_2CHCH_3)$ and n is from 1 to 4.

13. The composition of claim 10, wherein said cosurfactant is dipropylene glycol monomethyl ether.

14. The composition of claim 10, wherein said cosurfactant is diethylene glycol monobutyl ether.

* * * * *